US012653924B2

(12) United States Patent
Ou et al.

(10) Patent No.: US 12,653,924 B2
(45) Date of Patent: Jun. 16, 2026

(54) APPLICATION OF TOPICAL SKIN ADHESIVE TO SURGICAL MESH

(71) Applicant: Cilag GmbH International, Zug (CH)

(72) Inventors: Duan Li Ou, Warren, NJ (US); Julian Quintero, Flemington, NJ (US)

(73) Assignee: Cilag Gmbh International, Zug (CH)

( * ) Notice: Subject to any disclaimer, the term of this patent is extended or adjusted under 35 U.S.C. 154(b) by 574 days.

(21) Appl. No.: 17/991,992

(22) Filed: Nov. 22, 2022

(65) Prior Publication Data

US 2024/0165292 A1 May 23, 2024

(51) Int. Cl.
| | |
|---|---|
| *A61L 15/58* | (2006.01) |
| *A61F 2/00* | (2006.01) |
| *A61F 13/84* | (2006.01) |
| *A61F 13/00* | (2006.01) |

(52) U.S. Cl.
CPC .......... *A61L 15/585* (2013.01); *A61F 2/0063* (2013.01); *A61F 13/84* (2013.01); *A61F 2002/0068* (2013.01); *A61F 2013/00225* (2013.01); *A61F 2013/8497* (2013.01)

(58) Field of Classification Search
CPC ............ A61F 2/0063; A61F 2002/0068; A61F 2013/00225; A61F 2013/8497; A61F 13/00059; A61F 13/36
See application file for complete search history.

(56) References Cited

U.S. PATENT DOCUMENTS

| | | | |
|---|---|---|---|
| 2,399,545 A | | 4/1946 | Davis |
| 5,387,450 A | * | 2/1995 | Stewart ...................... C09J 7/35 |
| | | | 428/355 R |

| | | | |
|---|---|---|---|
| 5,861,348 A | | 1/1999 | Kas |
| 6,155,265 A | * | 12/2000 | Hammerslag ........ A61B 17/085 |
| | | | 128/898 |
| 6,599,525 B2 | | 7/2003 | Scamilla Aledo et al. |
| 8,097,008 B2 | | 1/2012 | Henderson |
| 8,579,922 B2 | * | 11/2013 | Glick ..................... A61B 90/94 |
| | | | 606/148 |
| 8,821,585 B2 | | 9/2014 | Pfeiffer et al. |

(Continued)

FOREIGN PATENT DOCUMENTS

| | | |
|---|---|---|
| EP | 3919032 A1 | 12/2021 |
| GB | 2425487 A | 11/2006 |

(Continued)

OTHER PUBLICATIONS

International Search Report and Written Opinion dated Feb. 15, 2024, for International Application No. PCT/IB2023/061723, 13 pages.

(Continued)

*Primary Examiner* — Julian W Woo

(74) *Attorney, Agent, or Firm* — Amir Bishara

(57) ABSTRACT

A system includes a surgical mesh having an upper side and a lower side, where the upper side includes a visual indicia pattern that extends longitudinally along the upper side, and the lower side is configured to adhere to a section of skin of a patient that surrounds a wound. The system further includes a topical skin adhesive configured to be applied to the upper side of the surgical mesh based on the visual indicia pattern. The topical skin adhesive is configured to cure within the surgical mesh to thereby form a protective layer over the wound.

17 Claims, 14 Drawing Sheets

(56) References Cited

U.S. PATENT DOCUMENTS

| | | | |
|---|---|---|---|
| 9,433,534 B2 | 9/2016 | Addison et al. | |
| 10,292,945 B2 | 5/2019 | Nierle et al. | |
| 10,729,807 B2 * | 8/2020 | Stewart | A61K 49/0054 |
| 10,842,707 B2 | 11/2020 | Robinson et al. | |
| 2005/0070956 A1 * | 3/2005 | Rousseau | A61B 17/085 |
| | | | 606/213 |
| 2010/0168633 A1 | 7/2010 | Bougherara et al. | |
| 2011/0038919 A1 | 2/2011 | Tauer et al. | |
| 2011/0082478 A1 | 4/2011 | Glick et al. | |
| 2014/0148640 A1 | 5/2014 | Thierfelder et al. | |
| 2017/0119515 A1 | 5/2017 | Priewe et al. | |
| 2019/0381207 A1 | 12/2019 | Jonn et al. | |
| 2021/0161720 A1 | 6/2021 | Kantrowitz et al. | |

FOREIGN PATENT DOCUMENTS

| | | | |
|---|---|---|---|
| TW | M387069 U | 8/2010 | |
| WO | WO 99/17906 A1 | 4/1999 | |

OTHER PUBLICATIONS

Muller, M., et al., "Transformation of tribological modelling of squeeze flows to simulate the flow of highly viscous adhesives and sealants in manufacturing processes," Proc Appl Math Mech, 2019, 19:e201900056, 2 pgs.

Polymer Science, Inc.—Pattern Coated Silicon Gel Adhesives, Aug. 2022, accessed from The Way Back Machine, https://polymerscience.com/pattern-coated-silicone-gel-adhesives/, 3 pgs.

Polymer Science, Inc.—P-DERM® Silcone Gel Adhesives, Brochure, May 2019, accessed from https://polymerscience.com/wp-content/uploads/2022/11/NEW-P-Derm-Silicone-Gel-Adhesives-Brochure-050719.pdf, 2 pgs.

\* cited by examiner

APPLICATION OF TOPICAL SKIN ADHESIVE TO SURGICAL MESH

BACKGROUND

A wound closure system (also referred to as a skin closure system) may be used at the conclusion of a surgical procedure on a patient to close a wound (e.g., a surgical incision) that was formed in the patient's skin for accessing a target anatomical structure. By way of example, wound closure systems may include components such as sutures, substrates, and/or liquid topical skin adhesives that are applied by a surgeon to approximate the edges of the wound and, in some cases, form a stable and protective layer over the wound that promotes efficient healing. In some instances, one or more components of the applied wound closure system may be absorbed by the patient during the healing process. Following healing of the wound, remaining components of the wound closure system may be removed from the skin by a surgeon, and/or they may automatically separate from the skin such that they may be discarded by the patient.

While various wound closure systems and associated components and methods have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the description given below, serve to explain the principles of the present invention.

Figure 1:
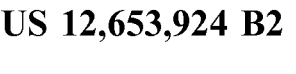
FIG. 1 depicts a perspective view of an example of a wound closure system that includes a wound closure device, an adhesive applicator, and an adhesive spreader.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "side," "upwardly," and "downwardly" also are used herein for reference to relative positions and directions. Such terms are used below with reference to views as illustrated for clarity and are not intended to limit the invention described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. WOUND CLOSURE SYSTEM

FIG. 1 shows an example of a wound closure system (10) that includes a wound closure device (20) (also referred to as a patch) configured to be applied to a patient's wound (W), an adhesive applicator (40) configured to apply a topical skin adhesive (54) (see FIG. 3D) to the applied wound closure device (20), and an adhesive spreader (60) configured to spread the applied topical skin adhesive (54) onto and through wound closure device (20). Each of these components is described in greater detail below.

Figure 2:
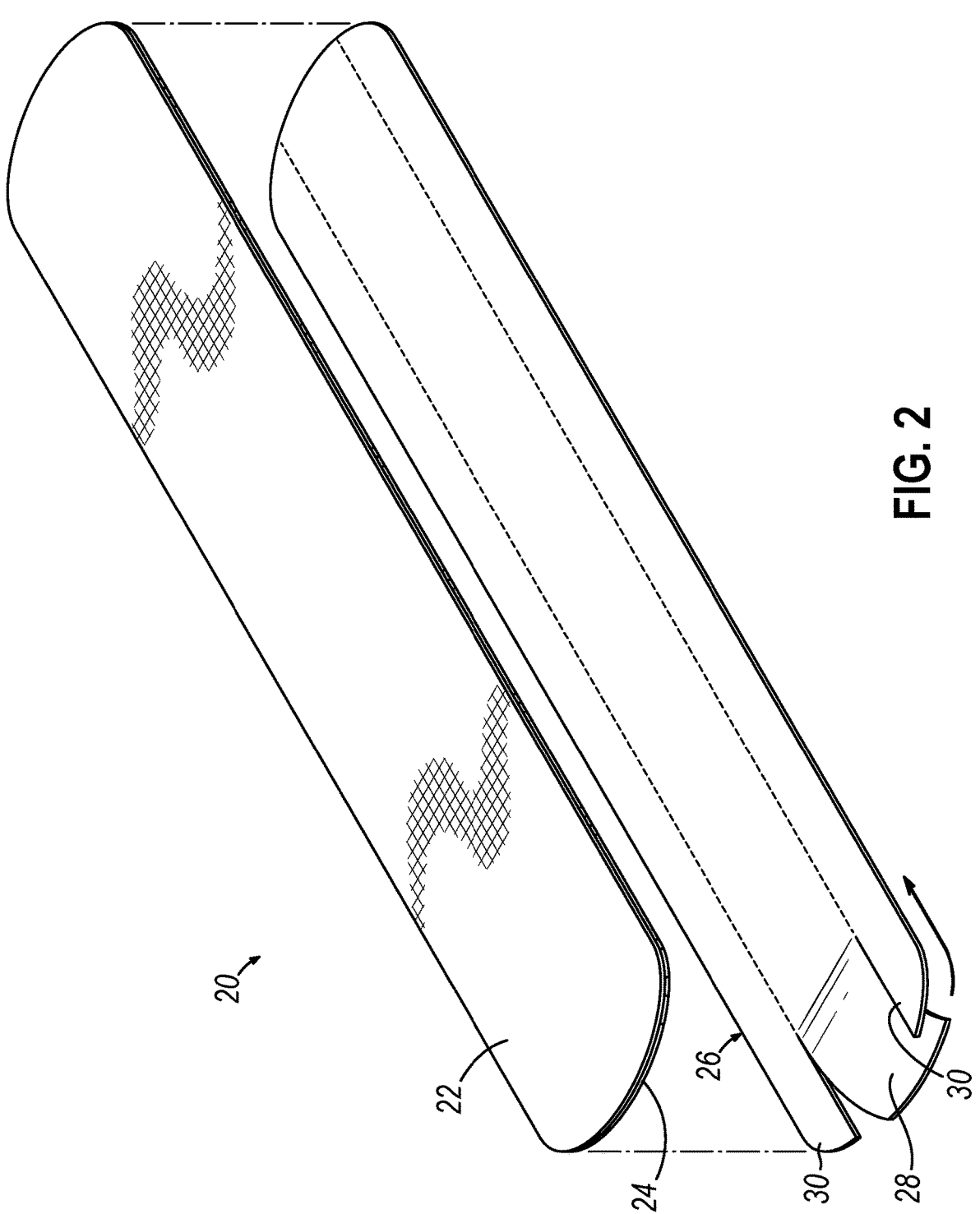
FIG. 2 depicts a disassembled perspective view of the wound closure device of FIG. 1, showing a mesh layer, a pressure sensitive adhesive layer, and a removable backing layer.

As shown best in FIG. 2, wound closure device (20) of the present version has an elongate, generally rectangular shape and a triple layer construction. More specifically, wound closure device (20) includes a layer of substrate in the form of a textile mesh (22), a layer of pressure sensitive adhesive (24) formed as a continuous or non-continuous coating along the lower skin-facing side of mesh (22), and a layer of backing (26) removably applied to the lower side of pressure sensitive adhesive (24). It will be understood that the term "wound closure device" as used herein encompasses wound closure device (20) both with and without backing (26), which may be removed and discarded during application of wound closure device (20) to a patient, as described in greater detail below.

Mesh (22) is configured to retain a liquid topical skin adhesive and may be formed of polyethylene (PET) or any other suitable surgical textile material. Pressure sensitive adhesive (24) is configured to enable wound closure device (20) to self-adhere to a patient's skin in response to a pressure being applied to the upper side of mesh (22) during its application by a surgeon. Backing (26) serves to protect pressure sensitive adhesive (24) before application of wound closure device (20) to the patient. In the present version, backing (26) includes elongate arrays of perforations that extend longitudinally and define an elongate central backing section (28) and a pair of elongate side backing sections (30). Though each backing section (28, 30) is shown as generally rectangular in the present version, backing sections (28, 30) may be of various alternative shapes, sizes, and quantities in other versions.

As shown in FIG. 1, adhesive applicator (40) includes an applicator body (42), a plunger unit (44) slidably received within an open proximal end of applicator body (42), and a static mixer (46) secured to a distal end of applicator body (42). Applicator body (42) includes a pair of barrels (48) arranged side by side, where each barrel (48) houses a respective part of a two-part liquid topical skin adhesive. Plunger unit (44) includes a pair of plungers (50) that are arranged side by side and are interconnected at their proximal ends by a bridge (52). Each plunger (50) is actuatable distally through a respective barrel (48) of applicator body (42) to force the corresponding liquid adhesive part distally into static mixer (46). Static mixer (46) is configured to receive the first and second adhesive parts and direct them around and through a series of static baffles and passages (not shown) that mix the two adhesive parts together into a homogenous liquid adhesive (54) that is then dispensed through an open distal end of static mixer (46), as shown in FIG. 3D described below.

In the present version, liquid topical skin adhesive (54) is in the form of a silicone-based topical skin adhesive that is configured to cure on skin at body temperature in less than two minutes. Once cured, topical skin adhesive (54) remains elastomeric such that a given section of cured adhesive (54) is configured to stretch up to 160% of its cured length and then fully recover to the cured length. Accordingly, wound closure system (10) may be particularly effective for use on actuatable body parts of a patient such as a knee, wrist, elbow, or other joint, for example.

As also shown in FIG. 1, adhesive spreader (60) of the present version has a monolithic body that includes a proximal body portion (62) configured to be gripped by a user, a distal body portion (64) that terminates at a tip configured to spread applied topical skin adhesive (54), and an intermediate flexural body portion (66) that interconnects the proximal and distal body portions (62, 64). Flexural body portion (66) is configured to elastically deform so that distal body portion (64) angularly deflects relative to proximal body portion (62) to promote effective spreading of topical skin adhesive (54) along wound closure device (20) with a suitable normal force within a predetermined range.

FIGS. 3A-3D show an example of wound closure system (10) being used to close a wound (W) formed in the skin (S) of a patient. In some procedures, wound (W) may be at least partially closed with one or more sutures, for example at deeper portions of wound (W), prior to use of wound closure system (10). Additionally, before wound closure device (20) is applied to the patient, it may be trimmed by a surgeon to any suitable shape as desired.

Figure 3A:
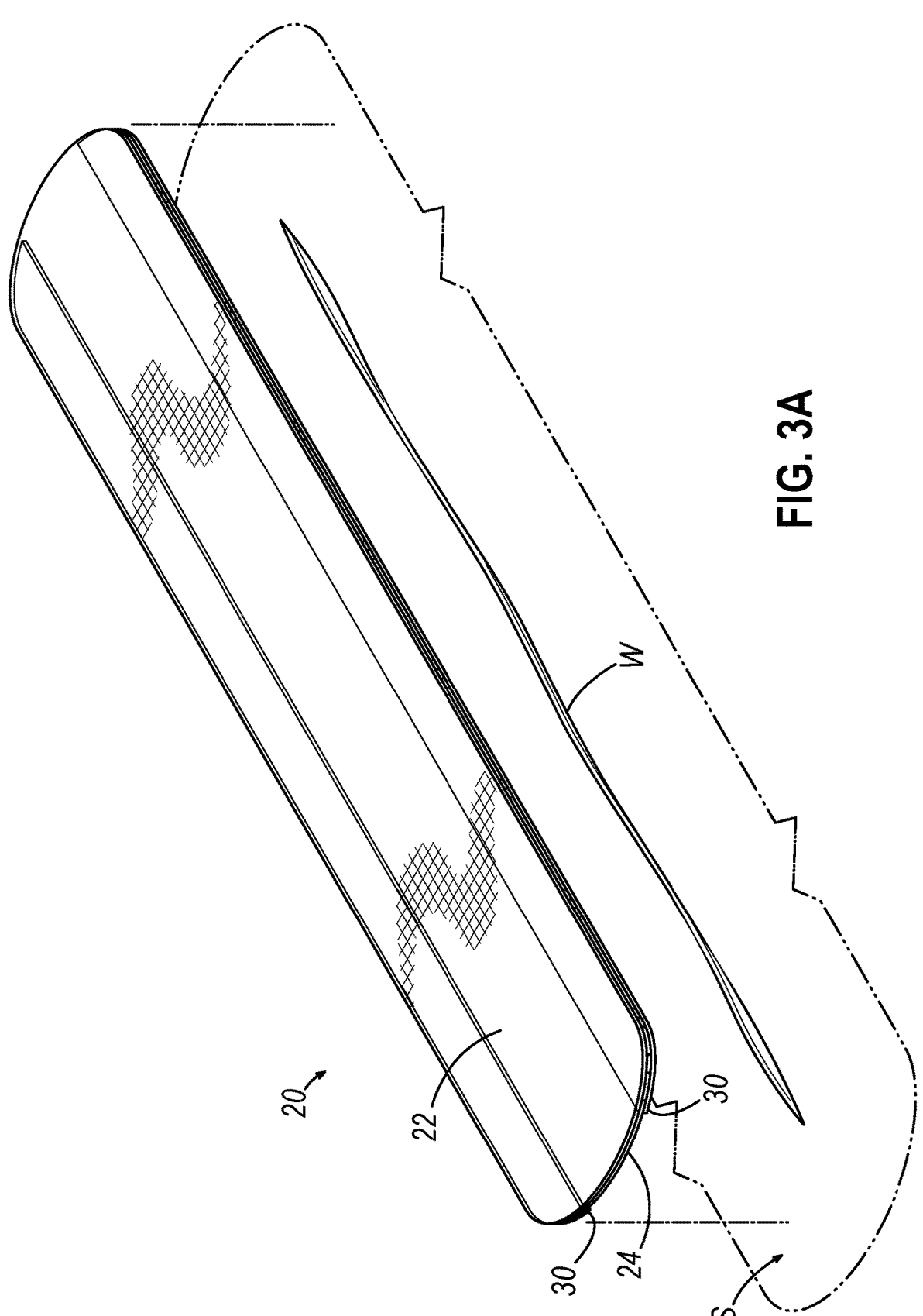
FIG. 3A depicts a perspective view of the wound closure device of FIG. 1 aligned longitudinally with a wound in the skin of a patient, showing a central section of the backing layer having been removed.
Figure 3B:
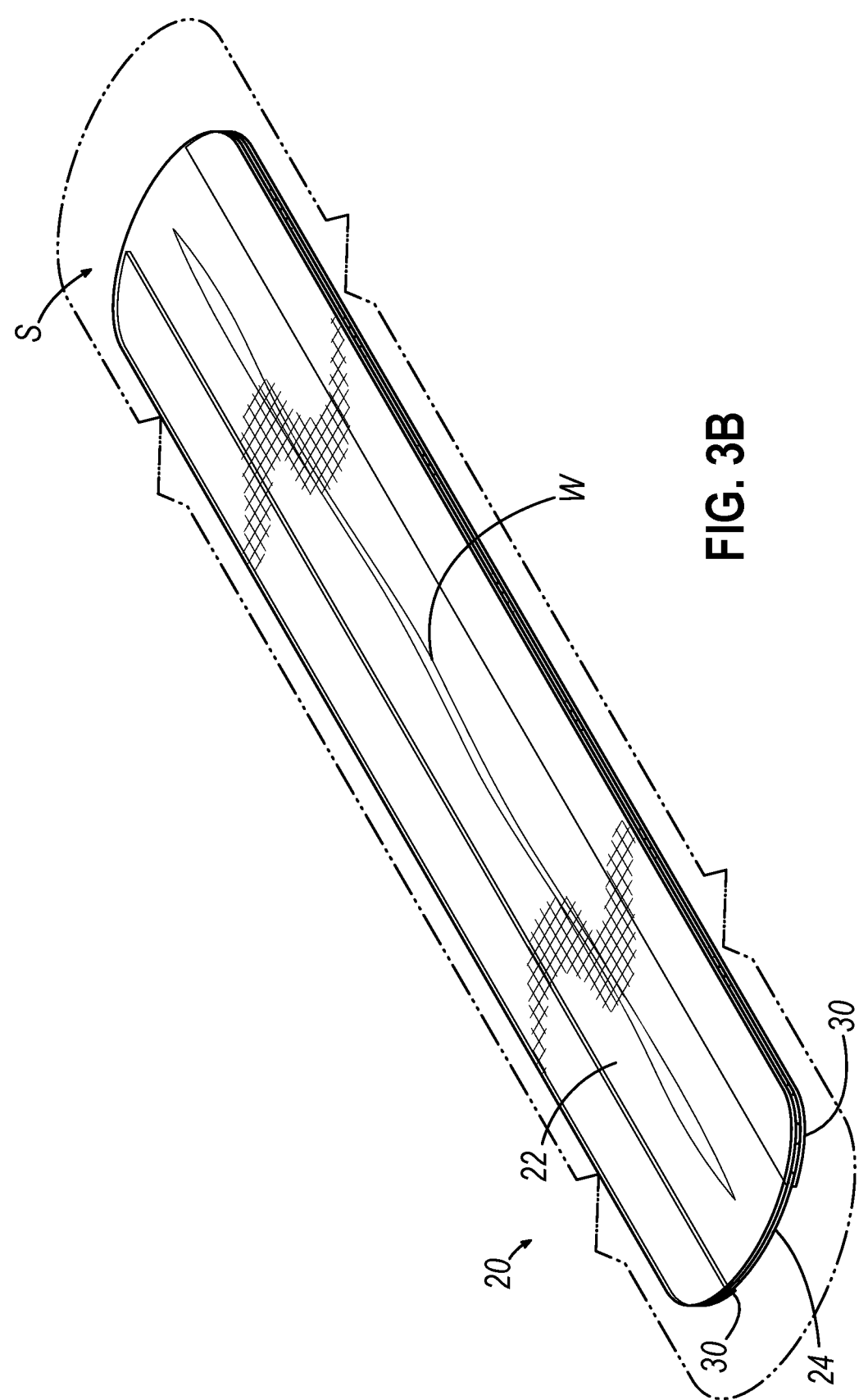
FIG. 3B depicts a perspective view of the wound closure device of FIG. 1 applied to the patient's skin over the wound to approximate the edges of the wound.
Figure 3C:
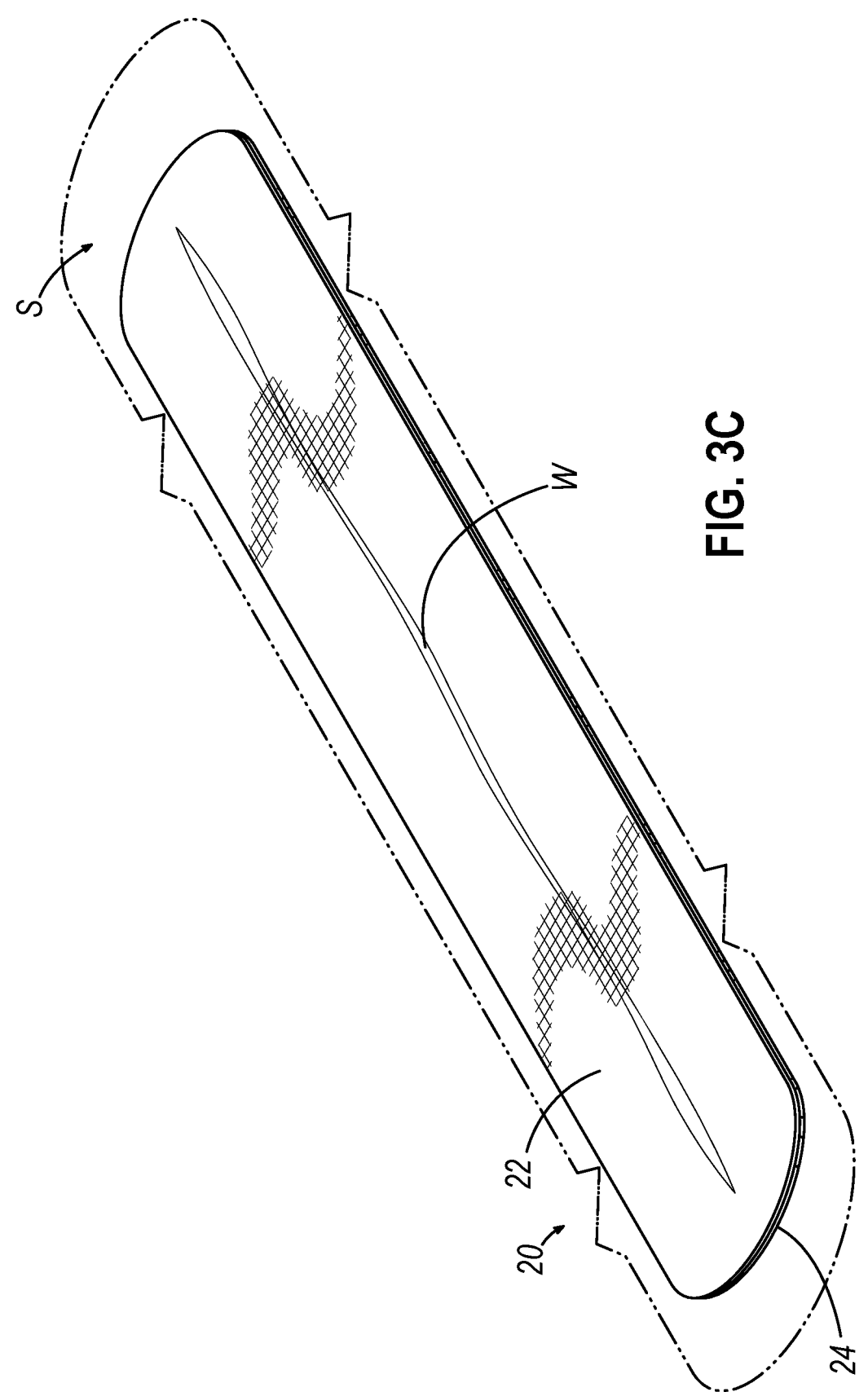
FIG. 3C depicts a perspective view of the wound closure device of FIG. 1 applied to the patient's skin over the wound, showing remaining sections of the backing layer having been removed so the wound closure device is fully adhered to the skin.
Figure 3D:
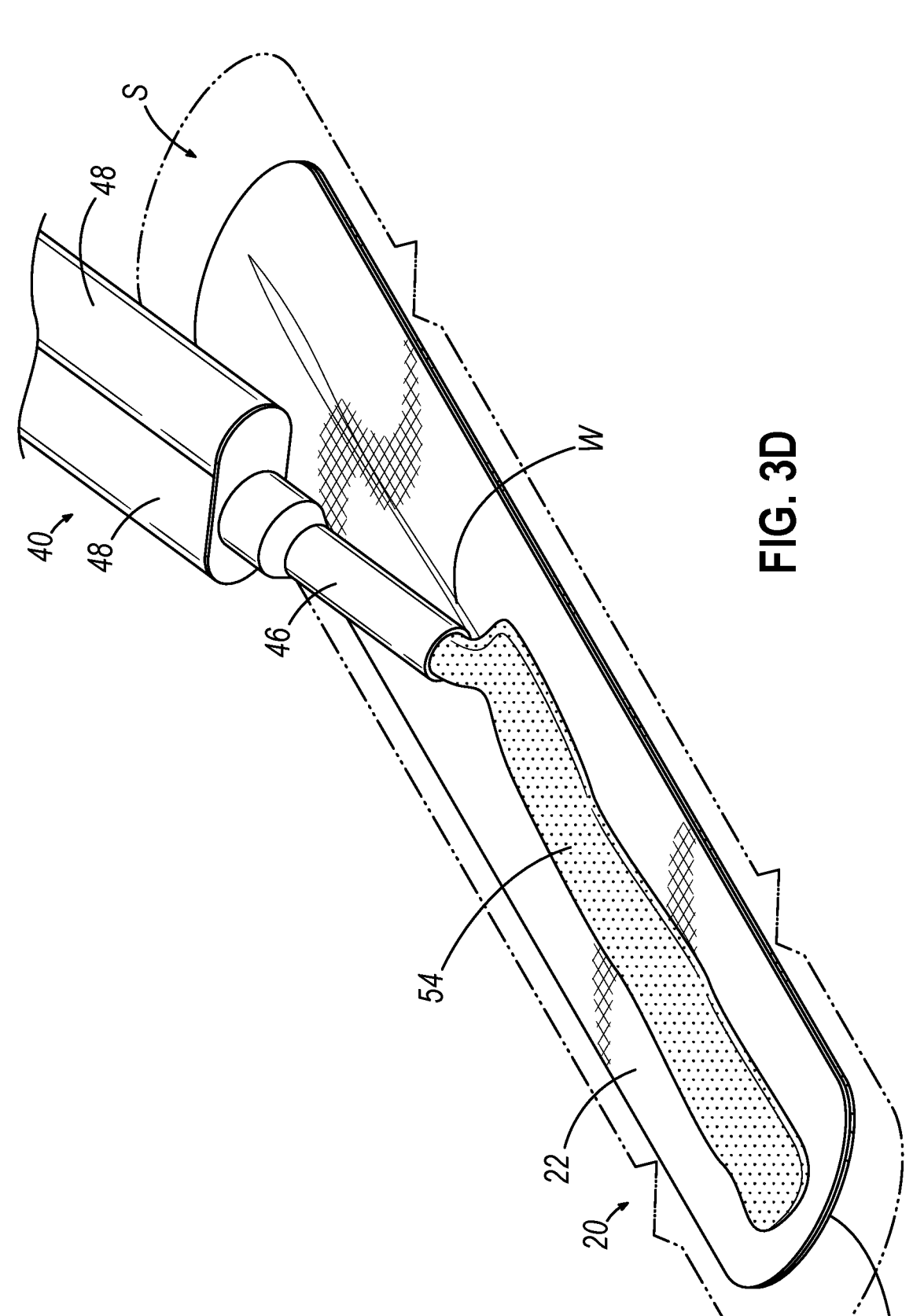
FIG. 3D depicts a perspective view of the wound closure device of FIG. 1 applied to the patient's skin over the wound, showing application of a liquid topical skin adhesive onto the mesh layer with the adhesive applicator.

As shown in FIG. 3A, central backing section (28) is removed from wound closure device (20) to expose a central window of mesh (22) and pressure sensitive adhesive (24), and an imaginary centerline of wound closure device (20) is aligned longitudinally with the edges of wound (W). Wound closure device (20) is then applied to the patient skin (S) over wound (W) and the surgeon applies pressure to the central portion of mesh (22) to force pressure sensitive adhesive (24) to adhere to the skin (S), thus fixing the edges of wound (W) relative to one another. Before this step, the edges of wound (W) may be held in an approximated state by the surgeon. Alternatively, during this step the central portion of wound closure device (20) may be applied in a laterally alternating manner to approximate the edges of wound (W) during application. With either approach, wound closure device (20) is configured to hold the edges of wound (W) in an approximated state following this initial step of application. Once the surgeon is satisfied with the position of wound closure device (20) relative to wound (W), the surgeon may then remove the remaining two side backing sections (30) to adhere the reminder of wound closure device (20) to skin (S).

As shown in FIG. 3D, adhesive applicator (40) is then used to apply a pattern of topical skin adhesive (54) to the upper side of mesh (22) of the applied wound closure device (20). While adhesive applicator (40) is shown applying a linear bead of topical skin adhesive (54) in the present version, it will be appreciated that various other patterns of topical skin adhesive (54) may be applied in other versions, such as a T-shaped pattern or a wave-shaped pattern, as described in greater detail below.

Figure 3E:
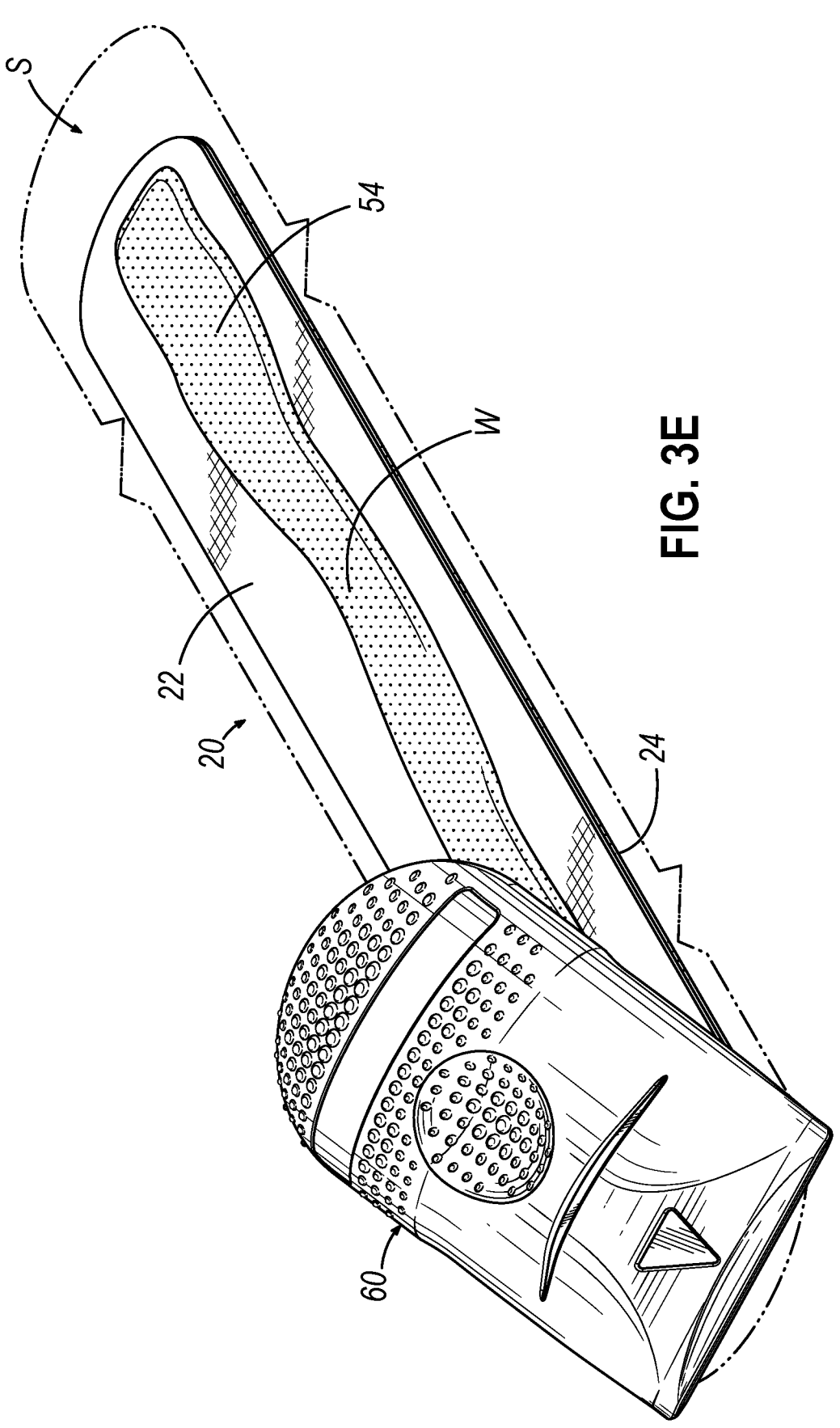
FIG. 3E depicts a perspective view of the wound closure device of FIG. 1 applied to the patient's skin over the wound, showing the adhesive spreader positioned against the patient at the start of an adhesive spreading stroke for spreading the applied topical skin adhesive over and through the wound closure device.
Figure 3F:
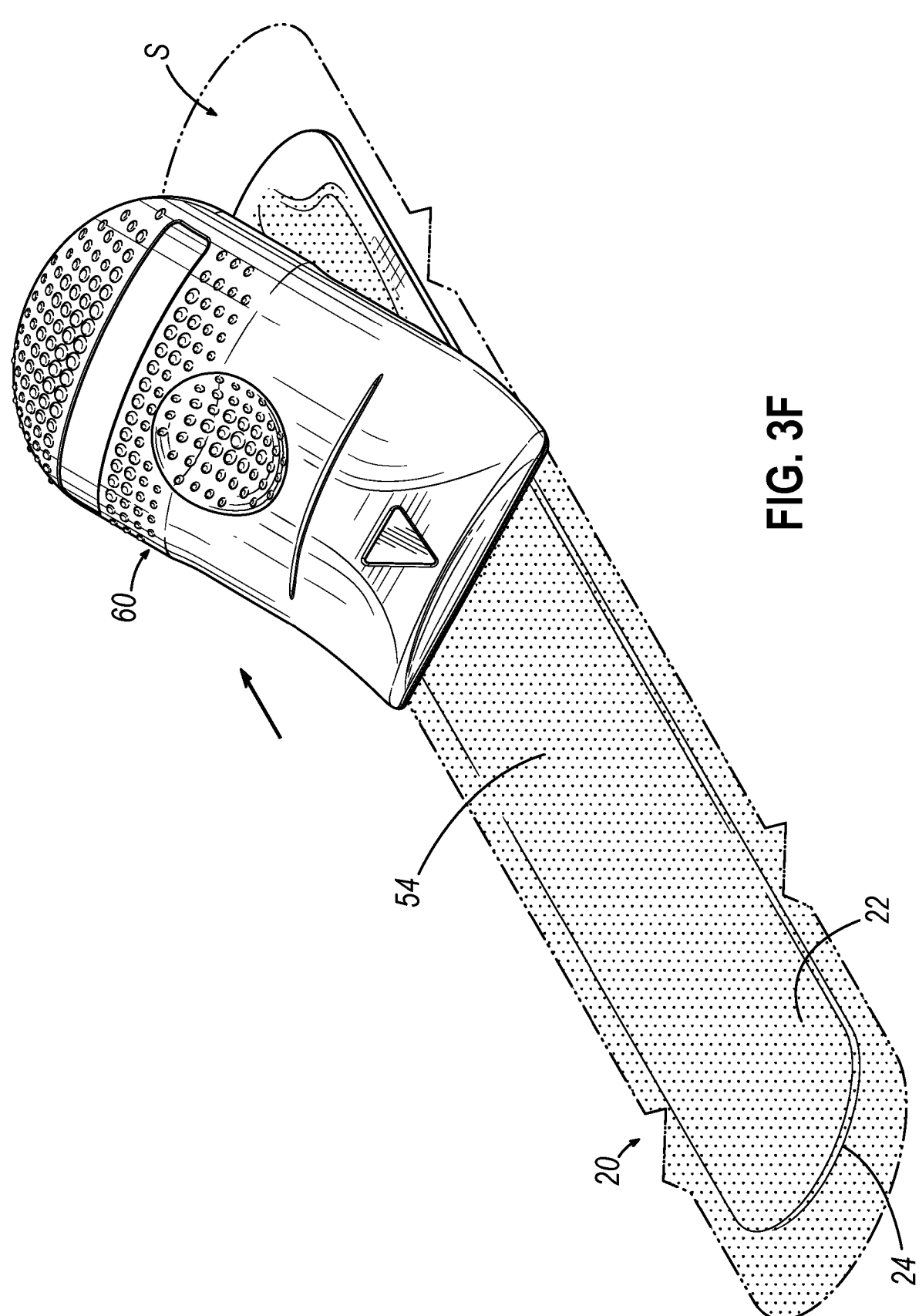
FIG. 3F depicts a perspective view of the wound closure device of FIG. 1 applied to the patient's skin over the wound, showing the adhesive spreader during a subsequent portion of the adhesive spreading stroke.

As shown in FIGS. 3E-3F, adhesive spreader (60) is then used to spread the applied topical skin adhesive (54) uniformly over wound closure device (20) to force the topical skin adhesive (54) through the layers of mesh (22) and pressure sensitive adhesive (24) and directly against wound (W) and the surrounding skin (S). In that regard, the layers of mesh (22) and pressure sensitive adhesive (24) may be at least partially permeable to permit forced passage of topical skin adhesive (54) therethrough. As shown in FIG. 3E, flexural body portion (66) of adhesive spreader (60) may be in a non-deformed state when adhesive spreader (60) is first positioned against wound closure device (20) at the beginning of an adhesive spreading stroke. As adhesive spreader (60) is dragged longitudinally along wound closure device (20), the input force exerted by the user may cause flexural body portion (66) to elastically deform such that distal body portion (64) angularly deflects relative to proximal body portion (62), as shown in FIG. 3F. The degree of deformation of flexural body portion (66) may be directly related to the viscosity of topical skin adhesive (54). In particular, a greater viscosity may require that the user exert a greater input force through proximal body portion (62) to effectively spread topical skin adhesive (54) over and through wound closure device (20), such that the flexural body portion (66) deforms a relatively greater amount. Conversely, a lesser viscosity may require a lesser input force such that the flexural body portion (66) deforms less or not at all.

Optionally, topical skin adhesive (54) may also be spread over adjacent portions of skin (S) not covered by wound closure device (20) to ensure that an entirety of mesh (22) is embedded with topical skin adhesive (54). For instance, and by way of example only, topical skin adhesive (54) may be spread onto at least 1 cm of skin (S) about the entire outer perimeter of the applied wound closure device (20). Once topical skin adhesive (54) has been fully spread over wound closure device (20), any topical skin adhesive (54) on skin (S) beyond the perimeter of device (20) may then be wiped away with sterile gauze, for example. Additionally, in some instances, a quantity of topical skin adhesive (54) may be applied between the edges of wound (W) before wound closure device (20) is applied to the skin (S). The applied topical skin adhesive (54) then cures within and over wound closure device (20) to form a composite microbial barrier over wound (W) that maintains a protective environment that promotes efficient healing. Following healing of wound (W), wound closure device (20) may be removed from the skin (S) manually (e.g., by a surgeon) or it may automatically separate from the skin (S) such that it may be discarded by the patient.

Wound closure system (10) may be further configured and operable in accordance with at least some of the teachings of U.S. Pat. Pub. No. 2021/0369258, entitled "Systems, Devices and Methods for Dispensing and Curing Silicone Based Topical Skin Adhesives," published Dec. 2, 2021, issued as U.S. Pat. No. 11,712,229 on Aug. 1, 2023, the disclosure of which is incorporated by reference herein, in its entirety; U.S. Pat. Pub. No. 2021/0371190, entitled "Systems, Methods and Devices for Aerosol Spraying of Silicone Based Topical Skin Adhesives for Sealing Wounds," published Dec. 2, 2021, issued as U.S. Pat. No. 11,518,604 on Dec. 6, 2022, the disclosure of which is incorporated by reference herein, in its entirety; U.S. Pat. Pub. No. 2021/0371658, entitled "Novel Topical Skin Closure Compositions and Systems," published Dec. 2, 2021, issued as U.S. Pat. No. 11,479,669 on Oct. 25, 2022, the disclosure of which is incorporated by reference herein, in its entirety; U.S. Pat. Pub. No. 2021/0369639, entitled "Novel Antimicrobial Topical Skin Closure Compositions and Systems," published Dec. 2, 2021, issued as U.S. Pat. No. 12,465,577 on Nov. 11, 2025, the disclosure of which is incorporated by reference herein, in its entirety; U.S. Pat. Pub. No. 2021/0369276, entitled "Anisotropic Wound Closure Systems," published Dec. 2, 2021, issued as U.S. Pat.

No. 11,589,867 on Feb. 28, 2023, the disclosure of which is incorporated by reference herein, in its entirety; and/or U.S. patent application Ser. No. 17/667,950, entitled "Gas Sterilizable Syringes Having Apertures Covered by Gas Permeable Barriers for Enabling Ingress and Egress of Sterilization Gases While Preventing Leakage of Flowable Materials," filed on Feb. 9, 2022, published as U.S. Pat. Pub. No. 2022/0395643 on Dec. 15, 2022, the disclosure of which is incorporated by reference herein, in its entirety.

II. EXAMPLES OF MESH WITH VISUAL INDICIA TO INDICATE ADHESIVE BEAD PATH

Once mixed, topical adhesive (54) can have a high viscosity (e.g., greater than 10,000 centipoise) relative to traditional cyanate acylate adhesive. This higher viscosity makes topical adhesive (54) unable to self-level on mesh (22) in the relatively short period of time after topical adhesive (54) is applied and before it begins to cure. Cure times may range between 1 and 2 minutes from application but may be shorter or longer. Given the inability of topical adhesive (54) to self-level and the short period of time with which to spread topical adhesive (54) before it begins curing, a system and method may be desirable to allow for fast and even spreading of topical adhesive (54) over mesh (22) and skin (S).

As described in greater detail below, FIGS. 4-8 show examples of alternative layers of mesh (122, 222, 322, 422, 522) that may be incorporated into wound closure device (20) in place of mesh (22). Each layer of mesh (122, 222, 322, 422, 522) includes a respective pattern of visual indicia (170, 270, 370, 470, 570) that is configured to serve as a traceable guide for applying topical skin adhesive (54) to wound closure device (20) with adhesive applicator (40). Visual indicia (170, 270, 370, 470, 570) may be printed, embossed, and/or debossed, for example, on mesh (122, 222, 322, 422, 522). Additionally, various combinations of the differing features of visual indicia (170, 270, 370, 470, 570) may be employed in other examples not illustrated in the drawings.

A. Mesh with Visual Indicia in the Form of a Wave

Figure 4:
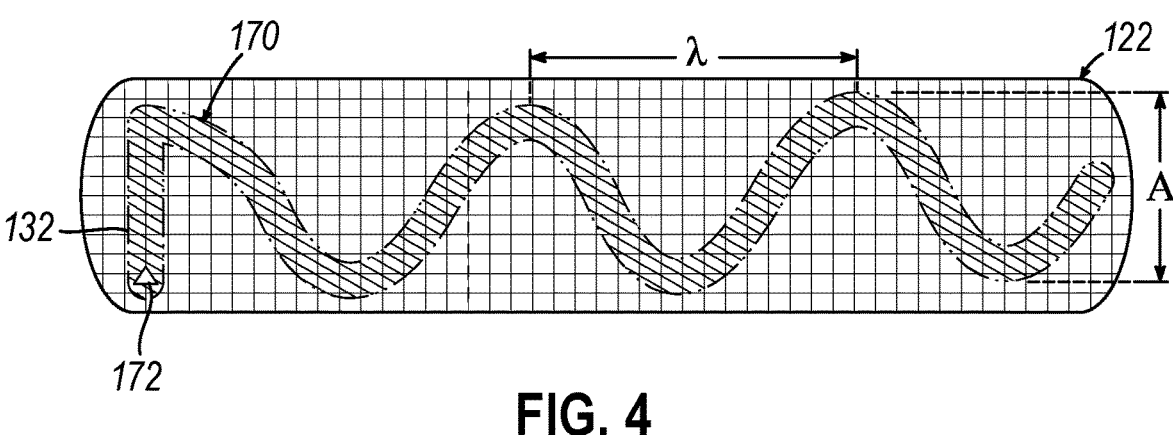
FIG. 4 depicts a top plan view of a mesh layer having visual indicia in the form of a wave.

As shown in FIG. 4, an upper side of mesh (122) may include visual indicia (170) which is configured to act as a visual guide when applying a bead of topical adhesive (54) to mesh (122). Visual indicia (170) of the present example is patterned to include a wave, which may be in the form of a sinusoid, and/or may include arcuate paths of various other similar shapes between longitudinal ends of mesh (122). The wave portion of visual indicia (170) may include any number of wavelengths ($\lambda$), each defined by a pair of adjacent peaks or troughs, and may extend up to an outer perimeter of the mesh (122) or may be inset from the outer perimeter of mesh (122). Wavelength ($\lambda$) may be consistent along a length of mesh (122) as shown, or it may vary across the length of mesh (122). An amplitude (A) of the wave may be approximately equal to or slightly less than a width of mesh (122) such that visual indicia (170) extends up to the outer perimeter of mesh (122) or is slightly inset from the outer perimeter of mesh (122). Amplitude (A) may be consistent along the length of mesh (122), or it vary across the length of mesh (122). By way of example only, amplitude (A) can range from 1.5 to 3 centimeters.

Visual indicia (170) may include one or more straight portions (132) at a first longitudinal end of mesh (122) as shown, where each straight portion (132) extends substantially the full width or a portion of the width of mesh (122).

Straight portion (132) may be configured to ensure that a larger initial amount of topical adhesive (54) is applied at the first longitudinal end of mesh (122). A larger initial amount of topical adhesive (54) at the longitudinal end of mesh (122) corresponding to the starting position of adhesive spreader (60) for a spreading stroke may aid in loading adhesive spreader (60) with topical adhesive (54) once spreading of topical adhesive (54) has commenced. Mesh (122) may include at least one directional indicator (172) which can indicate the preferred direction of travel when applying topical adhesive (54) to mesh (122). Directional indicator (172) may be incorporated into visual indicia (170) and may include one or more arrows, numbers, words, tick marks, other symbols, or any other indicator reasonable to indicate a direction of travel.

B. Mesh with Visual Indicia in the Form of a "T"

Figure 5:
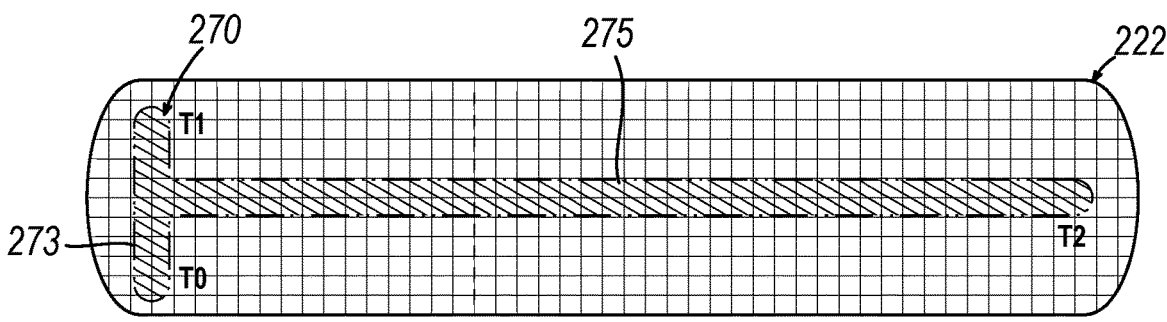
FIG. 5 depicts a top plan view of another mesh layer having visual indicia in the form of a "T" shape.

As shown in FIG. 5, an upper side of mesh (222) may include visual indicia (270) which is configured to act as a visual guide when applying a bead of topical adhesive (54) to mesh (222). Visual indicia (270) of the present example is patterned in the form of a "T" shape. A linear top portion (273) of the "T" may extend along a portion of a width of mesh (222) and is positioned either towards or at a longitudinal end of mesh (222), such as at the first longitudinal end of mesh (222) as shown. A linear shaft portion (275) of the "T" may extend directly over or adjacent and parallel to a longitudinal centerline of mesh (222). In doing so, visual indicia (270) may extend from a first longitudinal end of mesh (222) to a second longitudinal end of mesh (222) and may extend directly over top of and along the longitudinal centerline. In other versions, linear shaft portion (275) may be obliquely angled relative to and intersect the longitudinal centerline.

Mesh (222) may also include a series of time-based indicators (T0, T1, T2) spaced apart along visual indicia (270) to visually indicate a timeline for applying topical adhesive (54) to visual indicia (270). Time-based indicators (T0, T1, T2) may allow a user to gauge a rate for applying topical adhesive (54) in an effort to prevent pre-mature curing of topical adhesive (54) or applying topical adhesive (54) too quickly or too slowly such that a desired thickness of topical adhesive (54) is not achieved. In some versions, the timeline for time-based indicators (T0, T1, T2) may be linearly defined such that the amount of time to transition from each time-based indicator (T0, T1, T2) to the next is the same, such as one second for example. In other versions, the timeline may be nonlinear such that the amount of time to transition from time-based indicator (T0) to time-based indicator (T1) is a first duration, such as three seconds for example, whereas the amount of time to transition from time-based indicator (T1) to time-based indicator (T2) is a second duration, such as six seconds for example.

A preferred timeline for time-based indicators (T0, T1, T2) may be indicated in supporting device literature, such as instructions for use or package insert. Additionally, time based indicators (T0, T1, T2) themselves may visually indicate a preferred timeline. For example, it may be preferred to take one second to transition from time-based indicator (T0) to time-based indicator (T1), and an additional one second to transition from time-based indicator (T1) to time-based indicator (T2). In the illustrated example, this would produce a thicker bead of topical adhesive (54) along the shorter segment (273) of visual indicia (270) between time-based indicators (T0, T1), and a thinner bead of topical adhesive (54) along the longer segment (275) of visual indicia (270) between time-based indicators (T1, T2). In another example, time-based indicator (T2) may be replaced with a time-based indicator of a higher value, such as T6 for example, indicating a recommended duration of 5 seconds to transition from time-based indicator (T1) to time-based indicator (T6). In such an example, the beads of topical adhesive (54) applied along shorter indicia segment (273) between indicators (T0, T1) and along longer indicia segment (275) between indicators (T1, T6) may be approximately equal in thickness. In yet another example, mesh (222) may include a series of successive time-based indicators (T0, T1, T2, T3, T4, T5, T6, etc.) that are spaced apart equidistantly along visual indicia segments (273, 275).

It will be appreciated that various alternative quantities and arrangements of time-based indicators may be applied to mesh (222) beyond what is shown and described. Additionally, in some versions the time-based indicators may be configured to instruct application of discontinuous beads of topical adhesive (54), such that a constant adhesive bead (54) is not laid between all of the time-based indicators. It will also be appreciated that time-based indicators, such as those shown in FIG. 5 and described above, may be applied to any of the other exemplary meshes and visual indicia disclosed herein to facilitate proper application of topical adhesive (54).

C. Mesh with Visual Indicia in the Form of Vertical Lines

Figure 6:
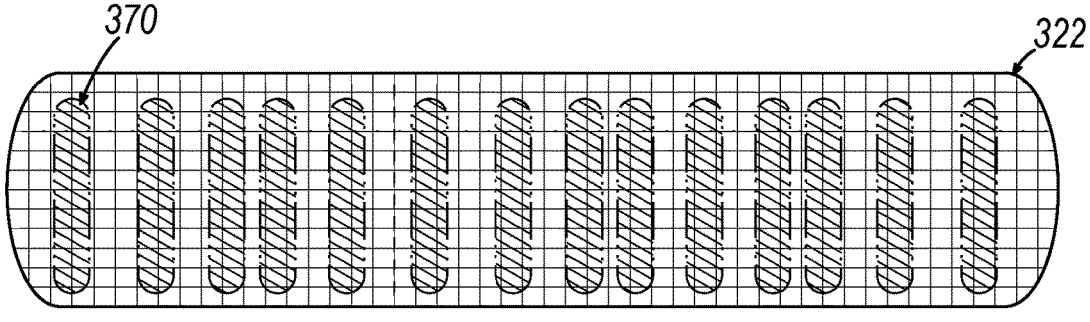
FIG. 6 depicts a top plan view of another mesh layer having visual indicia in the form of vertical lines.

As shown in FIG. 6, an upper side of mesh (322) may include visual indicia (370) which is configured to act as a visual guide when applying topical adhesive (54) to mesh (322). Visual indicia (370) of the present example is patterned in the form of a plurality of discrete vertical lines, each spanning along a width of mesh (322) and transversely to a length of mesh (322) such that they may be positioned perpendicular to a longitudinal centerline of mesh (322). In other versions, one or more of the lines may be angled obliquely relative to the longitudinal centerline. The vertical lines may extend along at least a portion of the width of mesh (322) and may be parallel to one another along the length of mesh (322). The vertical lines may be discrete pattern segments of visual indicia (370) that are disconnected and evenly spaced apart from one another along the entire length of mesh (322). Alternatively, the vertical lines may include uneven spacing, or may include a combination of even and uneven spacing. An example of a combination of even and uneven spacing may be exhibit vertical lines positioned closer together at a beginning portion of mesh (322) at its first longitudinal end, followed by vertical lines spaced further apart from one another in a direction advancing toward the opposed second longitudinal end of mesh (322). This spacing may be advantageous for initially loading adhesive spreader (60) with topical adhesive (54) and then, once adhesive spreader (60) is loaded, providing only enough topical adhesive (54) to evenly coat the remaining portions of mesh (322).

D. Mesh with Visual Indicia in the Form of Horizontal Lines

Figure 7:
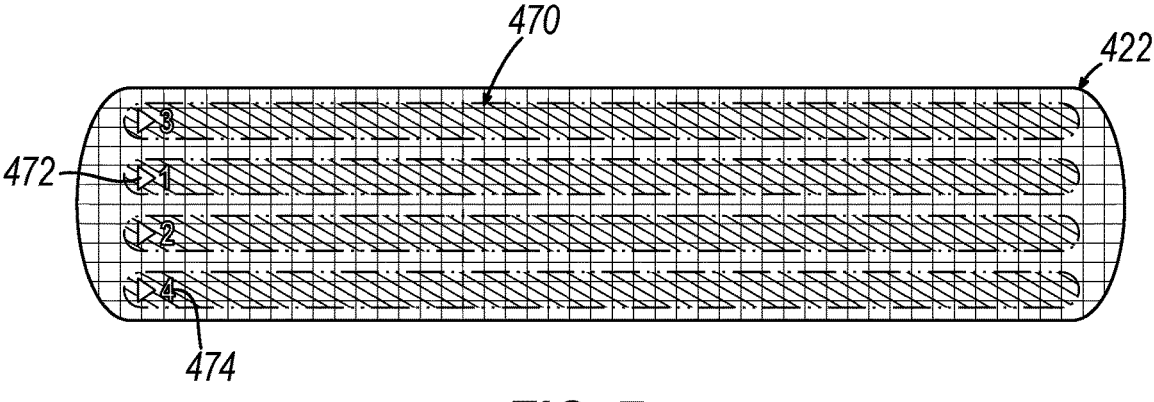
FIG. 7 depicts a top plan view of another mesh layer having visual indicia in the form of horizontal lines.

As shown in FIG. 7, an upper side of mesh (422) may include visual indicia (470) which is configured to act as a visual guide when applying topical adhesive (54) to mesh (422). Visual indicia (470) of the present example is patterned in the form of a plurality of discrete horizontal lines, each spanning a longitudinal length of mesh (422) and being parallel to a longitudinal centerline of mesh (422). In other versions, all or a portion of one or more of the lines may be angled obliquely relative to the longitudinal centerline. Each horizontal line may span the entire length of mesh (422), or one or more of the lines may be a different length from the other lines. The horizontal lines may be evenly spaced apart or may be unevenly spaced apart. Visual indicia (470) may further include a directional indicator (472) to indicate a direction in which each beads of topical adhesive (54) should be dispensed on mesh (422). Mesh (422) may also include application information (474) configured to indicate the order with which each bead should be dispensed on mesh (422). As an example, application information (474) may be in the form of numerical values that indicate that any middle horizontal line should be applied to mesh (422) prior to any outer horizontal lines. Applying middle horizontal lines to mesh (422) prior to outer horizontal lines may reduce the chance of adhesive applicator (40) coming into contact with an already laid bead of topical adhesive (54).

E. Mesh with Visual Indicia in the Form of a Triangle Wave

Figure 8:
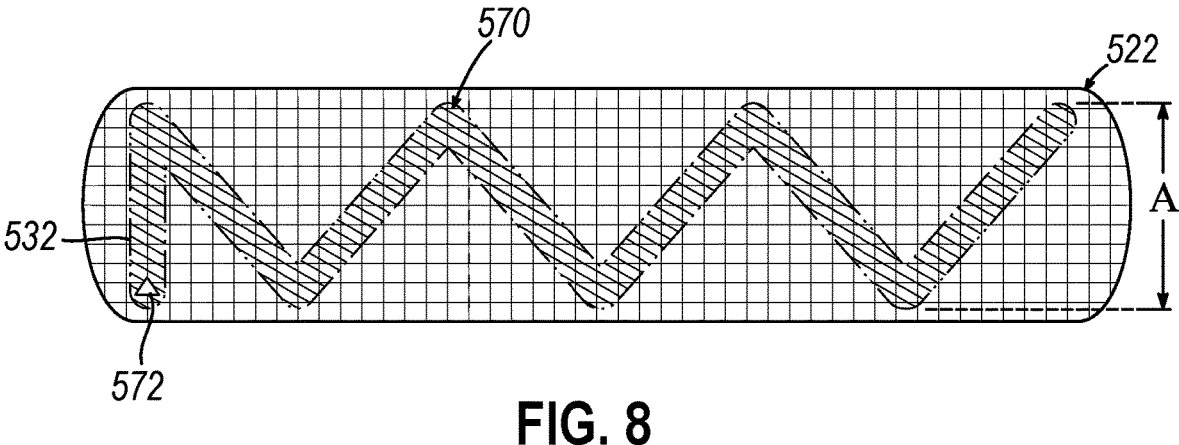
FIG. 8 depicts a top plan view of another mesh layer having visual indicia in the form of a triangle wave.

As shown in FIG. 8, an upper side of mesh (522) may include visual indicia (570) which is configured to act as a visual guide when applying topical adhesive (54) to mesh (522). Visual indicia (570) of the present example is patterned in the form of a triangle wave along a length of mesh (522). The triangle wave may include any number of wavelengths and may extend up to an outer perimeter of the mesh (522) or may be inset from perimeter of mesh (522). Wavelength may vary along a length of mesh (522). An amplitude of the triangle wave may be approximately equal to or slightly less than a width of mesh (522) such that visual indicia (570) extends up to the outer perimeter of mesh (522) or is slightly inset from the outer perimeter of mesh (522). The amplitude may be consistent along the length of mesh (522), or it may vary along the length of mesh (522). Visual indicia (570) may include one or more straight portions (532) at a first longitudinal end of mesh (522), where each straight portion (532) extends substantially the full width or a portion of the width of mesh (522). Straight portions (532) may be configured to ensure that a larger initial amount of topical adhesive (54) is applied at the first longitudinal end of mesh (522). As similarly noted above with respect to mesh (122), a larger initial amount of topical adhesive (54) at the longitudinal end of mesh (522) corresponding to the starting position of adhesive spreader (60) for a spreading stroke may aid in initially loading adhesive spreader (60) with topical adhesive (54) once spreading of topical adhesive (54) has commenced. Mesh (522) may include a directional indicator (572) which can indicate the preferred direction of travel when applying topical adhesive (54) to mesh (522). Directional indicator (572) may be incorporated into visual indicia (570) and may include one or more arrows, numbers, words, tick marks, other symbols, or any other indicator reasonable to indicate a direction of travel.

III. METHOD OF USE OF MESH WITH VISUAL INDICIA

Figure 9A:
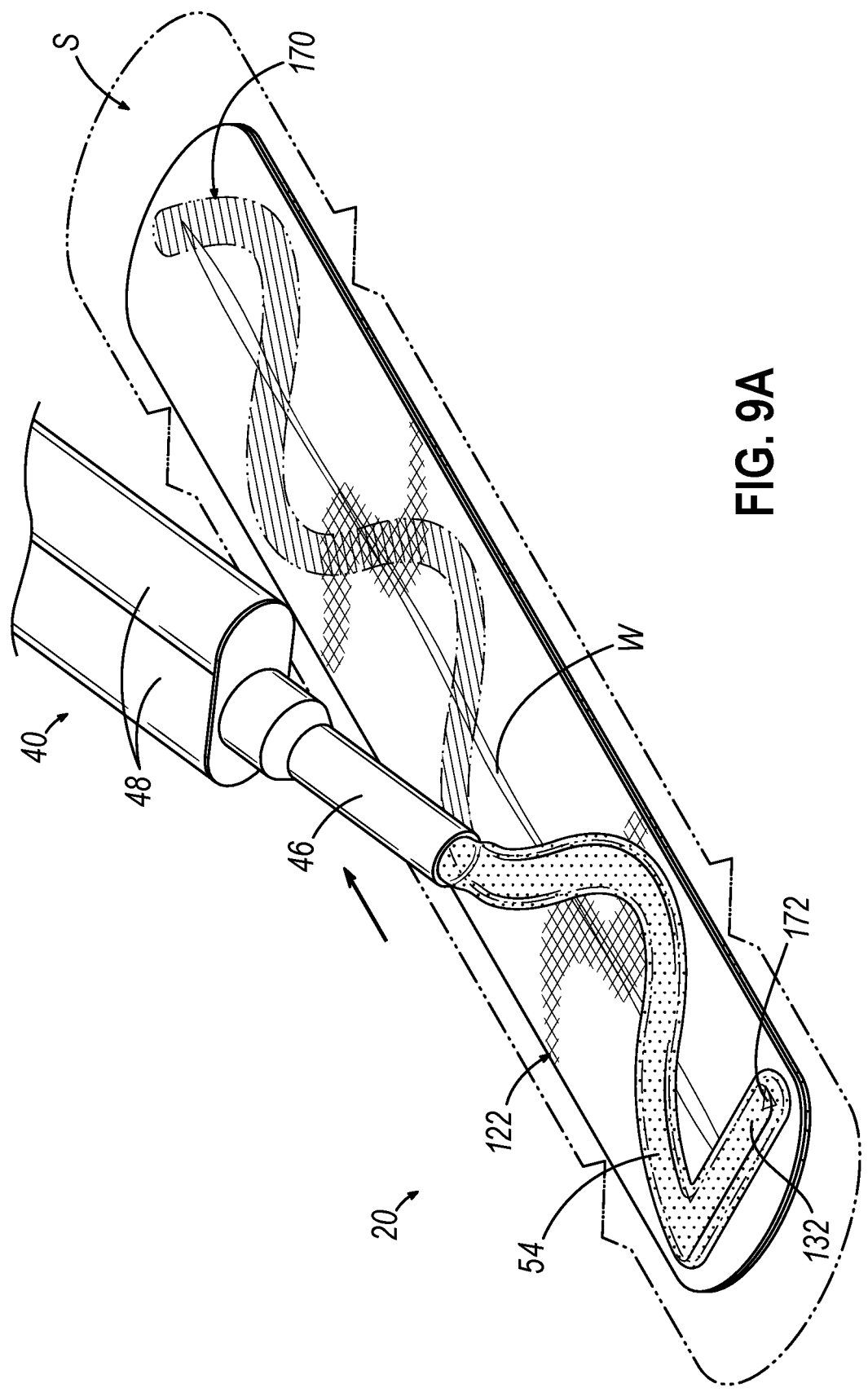
FIG. 9A depicts a perspective view of the wound closure device of FIG. 1 having the mesh layer of FIG. 4 applied to the patient's skin over the wound, showing an adhesive bead of topical skin adhesive being laid over the visual indicia of the mesh layer.
Figure 9B:
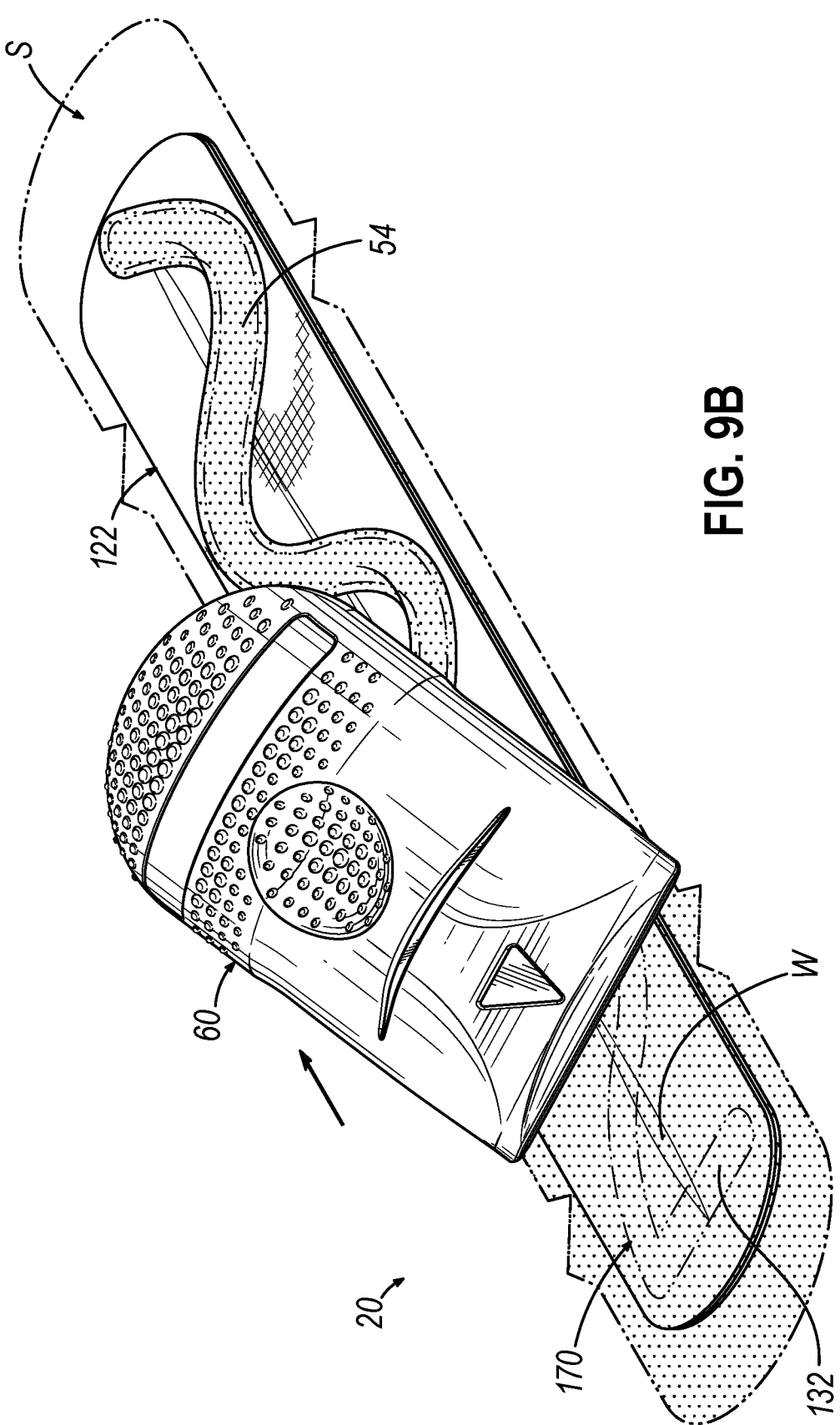
FIG. 9B depicts a perspective view of the wound closure device having the mesh layer of FIG. 4 applied to the patient's skin over the wound, showing the bead of topical skin adhesive over the visual indicia and with the adhesive spreader of FIG. 1 spreading the topical skin adhesive.
Figure 9C:
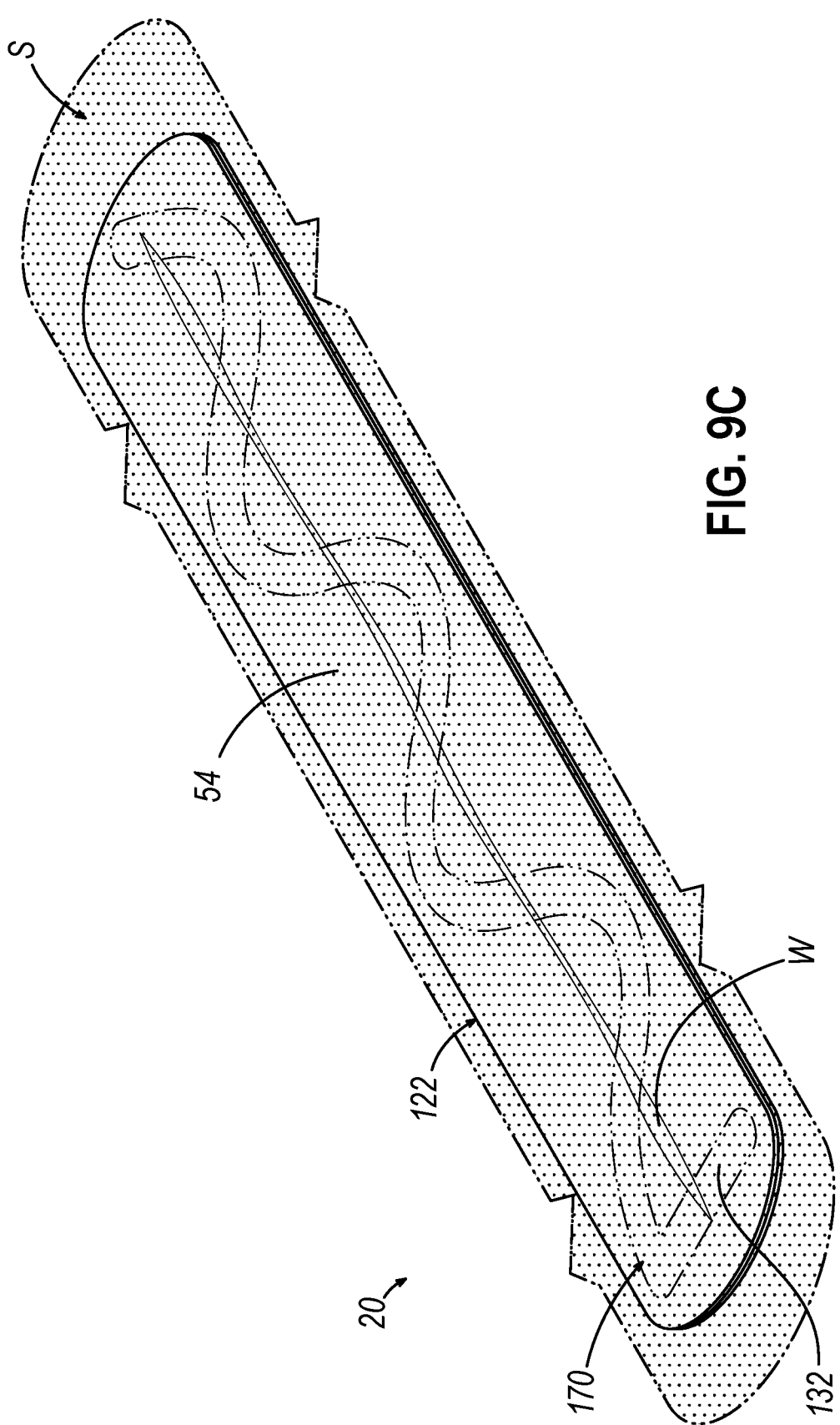
FIG. 9C depicts a perspective view of the wound closure device of FIG. 9A applied to the patient's skin over the wound, showing the topical skin adhesive spread over the mesh layer.

FIGS. 9A-9C show an example of wound closure system (10) having mesh (122) with the visual indicia (170) of FIG. 4 being used to close a wound (W) formed in skin (S) of a patient. It is understood that the visual indicia (170, 270, 370, 470, 570) of any mesh (122, 222, 322, 422, 522) of FIGS. 4-8 can be used in the below method.

As shown in FIG. 9A, the wound closure device (20) having mesh (122) with visual indicia (170) has been secured to skin (S) and wound (W) and backing (26) removed. Adhesive applicator (40) can be used to apply topical adhesive (54) to mesh (122). While applying topical adhesive (54), adhesive applicator (40) may follow (i.e., trace) visual indicia (170) such that a bead of topical adhesive (54) is applied over visual indicia (170). Adhesive applicator (40) may follow visual indicia (170) in a direction indicated by previously mentioned directional indicator (172). As discussed above in connection with visual indicia (170) of FIG. 4, the bead of topical adhesive (54) can be first applied to straight portion (132), which runs along at least a portion of the width of mesh (122) at its first longitudinal end (e.g., on the left-hand end as shown in the figures). As also discussed above, the portion of topical adhesive (54) applied to straight portion (132) of visual indicia (170) is engaged first by adhesive spreader (60) at the beginning of an adhesive spreading stroke in order to initially load adhesive spreader (60) with topical adhesive (54). Accordingly, topical adhesive (54) is applied to visual indicia (170) and is also spread by adhesive spreader (60) in the same direction of progression along the length of mesh (122) (e.g., from left to right in illustrated example). This approach may minimize the risk of any portion of the topical adhesive (54) applied to visual indicia (170) beginning to cure before it has been spread by adhesive spreader (60). Adhesive applicator (40) may apply topical adhesive (54) along visual indicia (170) in a direction indicated by directional indicator (172).

In versions of mesh (322, 422) having visual indicia (370, 470) arranged into discrete portions, adhesive applicator (40) may start and stop applying multiple topical adhesive (54) beads in order to cover each discrete portion separately. Adhesive applicator (40) may apply topical adhesive (54) along each discrete portion of visual indicia (370, 470) in a direction indicated by directional indicator (472). Adhesive applicator (40) may also apply topical adhesive (54) to each discrete portion of visual indicia (370, 470) in an order indicated by application information (474) where a specific discrete portion is applied prior to a separate discrete portion. For instance, adhesive applicator (40) may apply discrete portions of topical adhesive (54) from an inwardly-most discrete portion to an outwardly-most discrete portion according to mesh (322, 422) or may apply from one end of mesh (322, 422) to another end of mesh (322, 422), such as from one longitudinal end to an opposite longitudinal end.

As shown in FIG. 9B, adhesive spreader (60) is then used to spread the applied topical adhesive (54) uniformly over wound closure device (20) to force the topical adhesive (54) through mesh (122) and against wound (W). As shown in FIGS. 3E and 9B, adhesive spreader (60) may be pulled by the user through one or more longitudinal strokes along the length of mesh (122), parallel to its centerline. In other instances, adhesive spreader (60) may be directed along all or a portion of the path defined by visual indicia (170). Additionally, in some instances, topical adhesive (54) may also be spread over adjacent portions of skin (S) not covered by wound closure device (20) to ensure an effective seal about the outer perimeter of wound closure device (20).

Through applying topical adhesive (54) over visual indicia (170) of mesh (122), topical adhesive (54) can be spread evenly over wound closure device (20) in a rapid manner such that an even layer is applied over wound closure device (20) and surrounding skin (S) prior to topical adhesive (54) curing. For instance, the topical adhesive (54) could be applied to mesh (122) and spread evenly within approximately 30 seconds or less. As noted above, in some instances, a quantity of topical adhesive (54) may be applied between the edges of wound (W) before wound closure device (20) is applied to the skin (S). The spread topical adhesive (54) then cures within wound closure device (20) and against the skin (S) to form a composite microbial barrier over wound (W) that maintains a protective environment that promotes efficient healing. As shown in FIG. 9C, topical adhesive (54) may remain at least partially transparent after curing such that visual indicia (170) and/or wound (W) may be viewed through topical adhesive (54) once cured.

Figure 10:
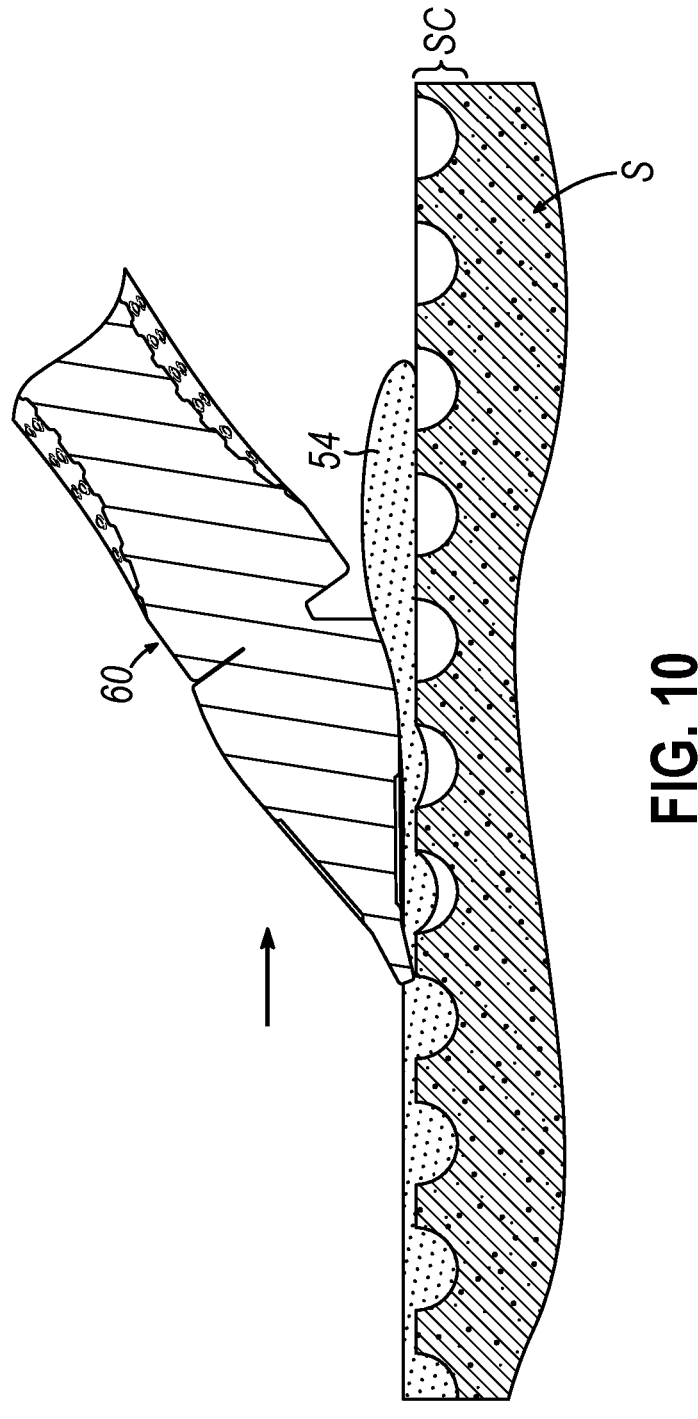
FIG. 10 depicts a cross-sectional view of a layer of a patient's skin, showing the topical skin adhesive being spread into a stratum corneum layer of the skin.

As shown in FIG. 10, adhesive spreader (60) may be capable of spreading and/or pushing topical adhesive (54) into a stratum corneum layer (SC) of the skin (S). This may increase adhesion and liquid resistance of topical adhesive (54) and wound closure device (20) over skin (S) and wound (W). Adhesive spreader (60) may be capable of applying topical adhesive (54) into the stratum corneum (SC) of the skin (S) either directly along the perimeter of wound closure device (20), or through wound closure device (20) (not shown).

In addition to or in place of having visual indicia (170, 270, 370, 470, 570) on any mesh (122, 222, 322, 422, 522), the pattern may be depicted in product instructions for use, package inserts, or other supporting materials that are made available to an operator.

IV. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising a surgical mesh including an upper side and a lower side, the upper side including a visual indicia pattern that extends longitudinally along the upper side, the lower side being configured to adhere to a section of skin of a patient that surrounds a wound; and a topical skin adhesive configured to be applied to the upper side of the surgical mesh based on the visual indicia pattern, the topical skin adhesive being configured to cure within the surgical mesh to thereby form a protective layer over the wound.

Example 2

The system of Example 1, wherein the surgical mesh is configured to adhere to opposing sides of the wound of the patient to thereby approximate the opposing sides.

Example 3

The system of any of the preceding Examples, further comprising a spreader configured to spread the topical skin adhesive across the upper side.

Example 4

The system of any of the preceding Examples, wherein the surgical mesh includes a first longitudinal end, a second longitudinal end, and a longitudinal centerline extending therebetween, wherein a portion of the visual indicia pattern intersects the longitudinal centerline or extends directly over top of and along the longitudinal centerline.

Example 5

The system of Example 4, wherein the visual indicia pattern extends from the first longitudinal end to the second longitudinal end.

Example 6

The system of any of the preceding Examples, wherein the visual indicia pattern includes a plurality of discrete pattern segments that are disconnected from one another.

Example 7

The system of any of the preceding Examples, wherein at least a portion of the visual indicia pattern extends along an arcuate path.

Example 8

The system of any of the preceding Examples, wherein the visual indicia pattern includes a sinusoidal wave.

Example 9

The system of any of the preceding Examples, wherein the visual indicia pattern includes a "T" shape.

Example 10

The system of any of Examples 4 through 9, wherein the visual indicia pattern includes a first line segment that transversely intersects the longitudinal centerline at the first longitudinal end, and a second line segment that extends directly over top of and along the longitudinal centerline from the first longitudinal end to the second longitudinal end.

Example 11

The system of any of the preceding Examples, wherein the visual indicia pattern includes a series of parallel lines.

Example 12

The system of Example 11, wherein at least some of the parallel lines extend parallel to the longitudinal centerline.

Example 13

The system of Example 11, wherein at least some of the parallel lines extend transversely to the longitudinal centerline.

Example 14

The system of any of the preceding Examples, wherein the surgical mesh includes a pressure sensitive adhesive along the lower side.

Example 15

The system of any of the preceding Examples, wherein the surgical mesh includes a plurality of time-based indicators collectively configured to visually indicate a timeline for applying topical skin adhesive to the upper side of the surgical mesh relative to the visual indicia pattern.

Example 16

A method, comprising: adhering the surgical mesh of Example 1 to a section of skin of a patient such that the surgical mesh overlies a wound in the skin; applying the topical skin adhesive of Example 1 onto the upper side of the surgical mesh with an adhesive applicator by tracing the visual indicia pattern with a dispensing tip of the adhesive applicator; and spreading the applied topical skin adhesive across the upper side and onto adjacent portions of the skin to thereby form a protective layer over the wound.

Example 17

A system, comprising: a surgical mesh including an upper side and a lower side, the upper side including a visual indicia pattern that extends longitudinally along the upper side, the lower side including a pressure sensitive adhesive configured to adhere to a section of skin of a patient that surrounds a wound; a topical skin adhesive configured to be applied to the upper side of the surgical mesh based on the visual indicia pattern, the topical skin adhesive being configured to cure within the surgical mesh to thereby form a liquid-resistant layer over the wound; and a spreader configured to spread the applied topical skin adhesive across the upper side prior to curing.

Example 18

A method, comprising: adhering a lower side of a surgical mesh to a section of skin of a patient such that the surgical mesh overlies a wound in the skin, wherein an upper side of the surgical mesh includes a visual indicia pattern that extends longitudinally along the upper side; applying a topical skin adhesive onto the upper side of the surgical mesh with an adhesive applicator by tracing the visual indicia pattern with a dispensing tip of the adhesive applicator; and spreading the applied topical skin adhesive across the upper side with a spreader, wherein the spread topical skin adhesive is configured to cure to thereby form a protective layer over the wound.

Example 19

The method of Example 18, the surgical mesh including a pressure sensitive adhesive along the lower side, wherein adhering the surgical mesh to the skin of the patient includes applying a pressure to the pressure sensitive adhesive.

Example 20

The method of any of Examples 18 through 19, wherein spreading the topical skin adhesive includes pushing the topical skin adhesive into cavities of a stratum corneum of the skin.

V. MISCELLANEOUS

It is understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/427,132, entitled "Device for Spreading Topical Skin Adhesive," filed Nov. 22, 2022, now expired, the disclosure of which is incorporated by reference herein, in its entirety; U.S. patent application Ser. No. 17/991,945, entitled "Surgical Mesh Securing Device for Wound Closure System," filed Nov. 22, 2022, published as U.S. Pat. Pub. No. 2024/0164777 on May 23, 2024, the disclosure of which is incorporated by reference herein, in its entirety; and/or U.S. patent application Ser. No. 17/991, 850, entitled "Wound Closure System Having Microcannulaic Pathways," filed Nov. 22, 2022, published as U.S. Pat. Pub. No. 2024/0164950 on May 23, 2024, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DA VINCI® system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK® bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:
  (i) a surgical mesh including an upper side and a lower side, the upper side including a single visual indicia that extends longitudinally along the upper side, the lower side being configured to adhere to a section of skin of a patient that surrounds a wound, the surgical mesh defining a length and a width perpendicular to the length, a portion of the single visual indicia extending across a majority of the width, and another portion of the single visual indicia extending across a majority of the length; and
  (ii) a topical skin adhesive configured to be applied to the upper side of the surgical mesh based on the single visual indicia, the topical skin adhesive being configured to cure on the patient and within the surgical mesh to thereby form a protective layer over the wound, wherein the topical skin adhesive includes a liquid configured to spread across the upper side of the surgical mesh.

2. The system of claim 1, wherein the surgical mesh is configured to adhere to opposing sides of the wound of the patient to thereby approximate the opposing sides.

3. The system of claim 1, further comprising a spreader configured to spread the topical skin adhesive across the upper side.

4. The system of claim 1, wherein the surgical mesh includes a first longitudinal end, a second longitudinal end, and a longitudinal centerline extending therebetween, wherein a portion of the single visual indicia intersects the longitudinal centerline or extends directly over top of and along the longitudinal centerline.

5. The system of claim 4, wherein the single visual indicia extends from the first longitudinal end to the second longitudinal end.

6. The system of claim 4, wherein at least a portion of the single visual indicia extends along an arcuate path.

7. The system of claim 6, wherein the single visual indicia includes a sinusoidal wave.

8. The system of claim 4, wherein the single visual indicia includes a "T" shape.

9. The system of claim 8, wherein the single visual indicia includes a first line segment that transversely intersects the longitudinal centerline at the first longitudinal end, and a second line segment that extends directly over top of and along the longitudinal centerline from the first longitudinal end to the second longitudinal end.

10. The system of claim 8, wherein the surgical mesh further includes at least one time-based indicator along the "T" shape.

11. The system of claim 10, wherein the "T" shape includes a first line and a second line perpendicular to and in contact with the first line, wherein the at least one time-based indicator includes:
  (a) a first time-based indicator proximate a first terminal end of the first line,
  (b) a second time-based indicator proximate a second terminal end of the first line, and
  (c) a third time-based indicator proximate an end of the second line.

12. The system of claim 1, wherein the surgical mesh includes a plurality of time-based indicators collectively configured to visually indicate a timeline for applying topical skin adhesive to the upper side of the surgical mesh relative to the single visual indicia.

13. A system, comprising:
  (i) a surgical mesh including an upper side and a lower side, the upper side including a single visual indicia that extends longitudinally along the upper side, the upper side defining a length and a width perpendicular to the length, the single visual indicia including a "T" shape having a first line and a second line perpendicular to the first line, the first line extending across a majority of the width, the second line extending across a majority of the length, the lower side including a pressure sensitive adhesive configured to adhere to a section of skin of a patient that surrounds a wound;
  (ii) a topical skin adhesive configured to be applied to the upper side of the surgical mesh based on the single visual indicia, the topical skin adhesive being configured to cure within the surgical mesh to thereby form a liquid-resistant layer over the wound; and
  (iii) a spreader configured to spread the applied topical skin adhesive across the upper side prior to curing.

14. The system of claim 13, wherein the surgical mesh is configured to adhere to opposing sides of the wound of the patient to thereby approximate the opposing sides.

15. The system of claim 13, wherein the surgical mesh includes a first longitudinal end, a second longitudinal end, and a longitudinal centerline extending therebetween, wherein a portion of the single visual indicia intersects the longitudinal centerline or extends directly over top of and along the longitudinal centerline.

16. The system of claim 13, wherein the surgical mesh includes a plurality of time-based indicators collectively configured to visually indicate a timeline for applying topical skin adhesive to the upper side of the surgical mesh relative to the single visual indicia.

17. A system, comprising:
  (i) a surgical mesh including an upper side and a lower side, the upper side including a single visual indicia that extends longitudinally along the upper side, wherein the single visual indicia includes a "T" shape including a first line and a second line perpendicular to and in contact with the first line, wherein at least one of the first line or the second line extends across a majority of a length of the upper side, the lower side being configured to adhere to a section of skin of a patient that surrounds a wound; and (ii) a covering configured to engage the upper side of the surgical mesh based on the single visual indicia, the covering being configured to form a protective layer over the wound.

* * * * *